US005506201A

United States Patent [19]

McDermott et al.

[11] Patent Number: 5,506,201

[45] Date of Patent: Apr. 9, 1996

+

[54] FORMULATION OF A FAT SURFACTANT VEHICLE CONTAINING A FRAGRANCE

[75] Inventors: Keith J. McDermott, Bridgewater; John M. Teffenhart, Edison; Eric P. Guénin, Piscataway; Shmuel D. Shefer, East Brunswick; Chee-Teck Tan, Middletown; Leslie C. Smith, Plainsboro, all of N.J.

[73] Assignee: International Flavors & Fragrances Inc., New York, N.Y.

[21] Appl. No.: 346,217

[22] Filed: Nov. 22, 1994

Related U.S. Application Data

[63] Continuation-in-part of Ser. No. 235,716, Apr. 29, 1994, abandoned.

[51] Int. Cl.$^6$ .................................................... A61K 7/46

[52] U.S. Cl. ......................................... 512/4; 252/174.11

[58] Field of Search ............................ 512/4; 252/174.11

[56] References Cited

U.S. PATENT DOCUMENTS

| | | | |
|---|---|---|---|
| 4,209,417 | 6/1980 | Whyte | 252/174.11 |
| 4,405,509 | 9/1983 | Rogers et al. | 512/4 |
| 4,808,320 | 2/1989 | Jacques | 252/8.75 |
| 4,973,422 | 11/1990 | Schmidt | 252/174.11 |
| 5,188,753 | 2/1993 | Schmidt | 252/132 |

FOREIGN PATENT DOCUMENTS

| | | | |
|---|---|---|---|
| 0036720 | 9/1981 | European Pat. Off. | 512/3 |

*Primary Examiner*—James H. Reamer
*Attorney, Agent, or Firm*—Arthur L. Liberman

[57] ABSTRACT

A method is disclosed for producing a fragrance containing solid particle for incorporation into laundry detergent by selecting a fat component such as a fatty acid glyceride, heating said fat component to an elevated temperature sufficient to form a molten melt thereof, selecting a solid surface active agent from the group consisting of SPAN® surfactants with an HLB of 4.3 to 8.6, heating the surface active agent to form a molten melt thereof and then combining the melts with an aroma chemical to form a mixture. The melt is rapidly cooled to form a solid material.

3 Claims, 1 Drawing Sheet

FORMULATION OF A FAT SURFACTANT VEHICLE CONTAINING A FRAGRANCE

REFERENCE TO A RELATED APPLICATION

This application is a continuation-in-part of application Ser. No. 08/235,716 filed Apr. 29, 1994, now abandoned, which is relied on and incorporated herein by reference.

INTRODUCTION AND BACKGROUND

The present invention relates to a formulation of a fat and a solid surface active agent for use as a carrier for an aroma chemical or fragrance for the purpose of imparting a fragrance to a laundry detergent composition containing the fat/surface active agent formulation used to increase substantivity of fragrances on fabrics. In another aspect, the present invention relates to a method of formulating a fat and surface active agent carrier for one or more aroma chemicals.

The method of the present invention enables the production of fragrances containing solid particles of improved substantivity for use in a variety of laundry detergents.

It has been the practice in the past to impart fragrance to standard powdered laundry detergent by simply spraying the fragrance or aroma chemical onto the detergent base formulation. In such prior art developments, it is typical that the detergent contains at least 0.5% by weight of the fragrance formulation. In the course of the washing process wherein clothes are washed with the standard powdered laundry detergent, a very small fraction of the fragrance that is contained in the detergent is actually transferred to the clothes. Tests have shown that the amount of fragrance that is left as a residue on the clothes can be as low as 1% of the original small amount of fragrance that is contained in the detergent formulations itself. Hence, it will be seen that 1% of as little as 0.5% by weight fragrance is a very small amount of fragrance indeed.

One approach to solve this problem that has been used in the prior art is to employ a carrier to bring the fragrance to the clothes. The carrier is formulated to contain fragrance and to attach itself to the clothes during the washing cycle through particle entrainment or chemical charge.

The procedures of the prior art and formulations of the prior art have not been altogether successful because of the low substantivity of the fragrances. In the detergent industry the term "substantivity" refers to the deposition of the fragrance on the clothes and the retention and perception of the fragrance on the laundered clothing.

SUMMARY OF THE INVENTION

It is an object of the present invention to provide improved substantivity of fragrances by utilizing a suitable carrier to bring the fragrance to the laundered clothes.

It is a further object of the present invention to provide improved powdered laundry formulations which result in improved substantivity of fragrances.

In obtaining the above and other objects, one feature of the present invention resides in formulating a fat and solid surface active agent carrier for a fragrance to be used in a laundry detergent.

More particularly, the method of the invention for producing a fragrance containing solid particle of improved substantivity for incorporation into laundry detergents is carried out by:

(i) selecting a fat component from the group consisting of glycerol which is mono, di or tri substituted with a saturated or unsaturated organic moiety of 3 to 30 carbon atoms;

(ii) heating the fat component to an elevated temperature sufficient to form a first molten melt thereof;

(iii) selecting a solid surface active agent from the group consisting of a SPAN® surfactant of HLB 4.3 to 8.6;

(iv) heating the surface active agent to form a second molten melt thereof;

(v) combining the first and second melts with an aroma chemical and uniformly dispersing the aroma chemical in the combined melt of the fat component and the surfactant;

(vi) rapidly cooling the melts to form a solid material containing the fat component, the nonionic SPAN® surfactant and aroma chemical; and (vii) forming solid particles thereof to obtain a fragrance containing particulate aroma chemical carrier.

The SPAN® surfactant are defined as a mixture of compounds having the structure:

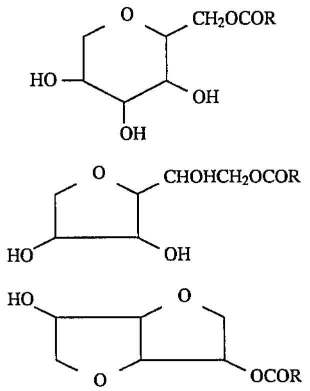

wherein R stands for fatty acid residues.

Generally, the fat component is present in the amount of 40 to 99% by weight, and the surfactant is present in the amount of 1 to 60% by weight, excluding the quantity of aroma chemical. Preferably, the aroma chemical is present in an amount of 1 to 40% by weight based on 100 parts by weight of combined fat component and surfactant.

It has been found useful for the fat component to contain 10 to 20 carbon atoms.

Preferably, the fat component is selected from natural fats obtained from solid waxy oils from soybean, palm, corn, cottonseed, safflower and coconut plant sources.

Typically, the fat has the formula:

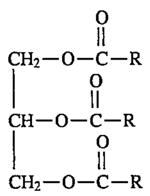

wherein R can be the same or different organic group containing 5 to 30 carbon atoms.

It is a further feature of the present invention to provide carrier matrices based on fat and surfactants for the fragrance which is carried to the laundered clothing.

BRIEF DESCRIPTION OF THE DRAWING

The present invention will be further understood with reference to the detailed description herein below taken together with FIG. 1 which shows a schematic flow diagram of the process of the invention.

DETAILED DESCRIPTION OF THE INVENTION

Figure 1:
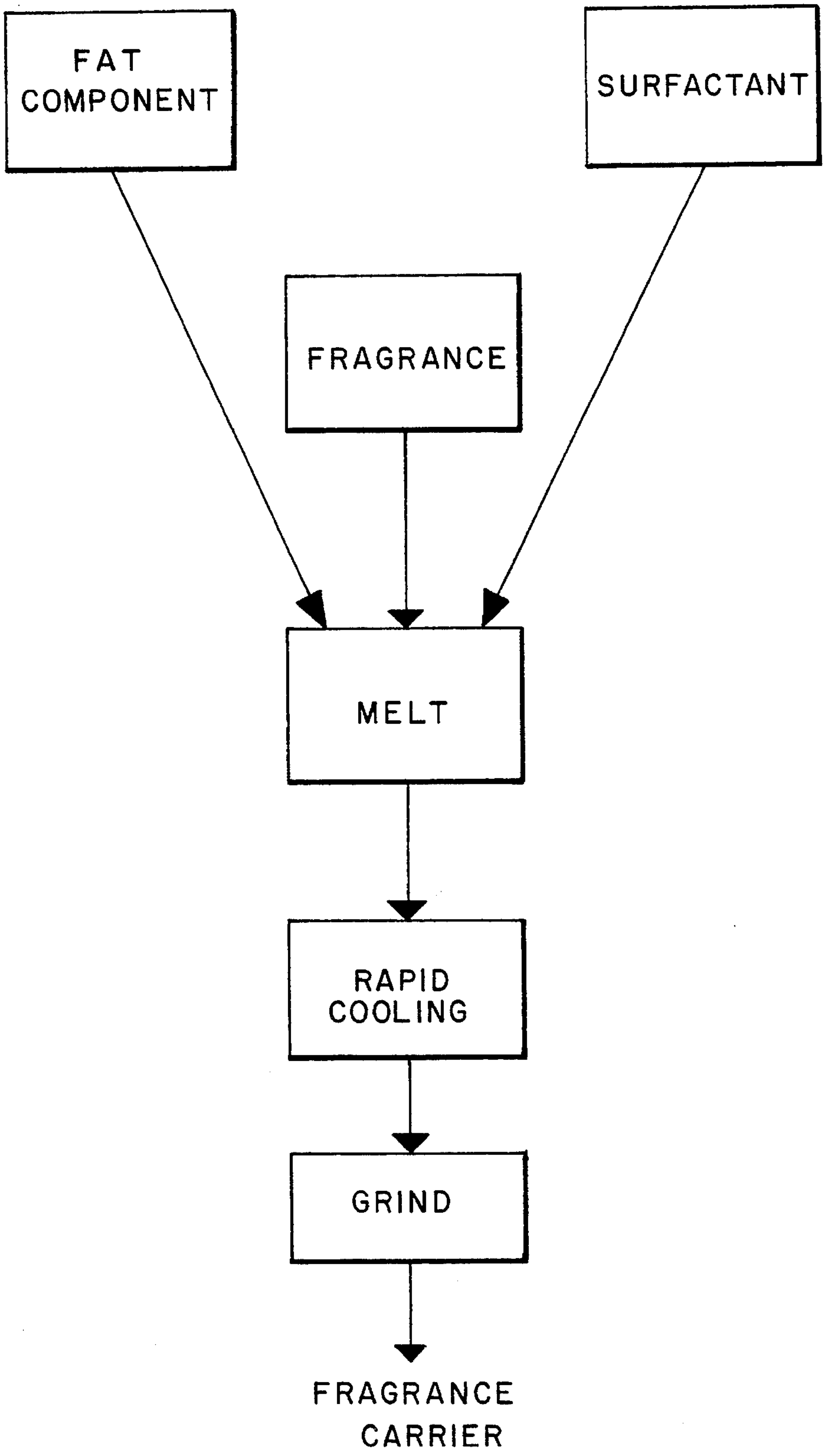

It has been found that improved substantivity of fragrances can be achieved by formulating a fat and solid surface active agent which is then introduced into a laundry detergent. By a careful selection of the fat and solid surface active agent, it is possible to achieve improved substantivity of the fragrance.

In carrying out the invention, the formulation of the fat and solid surface active agent is begun by selecting a fat component in the amount of 40 to 99% and combining it with a low HLB surfactant such as a fatty acid ester in the amount of 1 to 60%. It has been determined that the HLB value ranges from 4.3 to 8.6 in order to obtain the results described herein. These two components are melted by heating each to a sufficiently elevated temperature to form a melt and mixed at a temperature above the melting point of the highest melting component. To the resulting melt, there is then added one or more aroma chemicals to impart the desired fragrance in the amount of about 1 to 40% by weight based on 100 parts by weight of the molten mix of fat component and surfactant. After thorough mixing to ensure uniform dispersion of the aroma chemical in the fat/surfactant mixture to form a homogeneous mixture, the mixed components are subjected to fast cooling to yield a solid material which is the fat/surfactant fragrance carrier. This solid carrier is then ground to a suitable particle size and then mixed with a conventional laundry detergent base formulation to produce the final detergent formulation to be used by the customer.

One suitable method for making the fragrance carrier material is to premelt the fat component by heating at about 100° C. and the surfactant at about 70° C. Generally the melt is formed by heating the components above the melting temperature of the highest melting component. Any suitable heating equipment can be used for this purpose such as a scraped wall steam jacketed vessel. The two melts are then mixed together to ensure an adequate and uniform dispersion of both materials in each other. Suitable mixers known in the art can be used for this purpose. The aroma chemical or fragrance is then added and then mixed with the molten mixture. The molten mixture is then rapidly cooled on a suitable cooling apparatus such as chilled drums or cooled belt to produce a solid material. The product is then ground through a 2 mm screen in a conventional grinding apparatus such as a Cumberland mill with cryogenic cooling in order to remove the heat generated by grinding. The result is particles of about 1 mm in diameter.

Alternative methods for forming the final product particles can be used such as spray chilling, drum chilling and extrusion.

Examples of materials that can be used in accordance with the invention as the fat component are the following fatty materials:

triglycerides which are esters of saturated and unsaturated fatty acids.

Illustrative of these compounds are those represented by the formula:

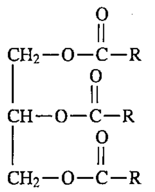

wherein R can be the same or different organic groups containing 5 to 30 carbons.

Surfactants suitable for purposes of the invention are those sold under the trademark SPAN® which are nonionic surface active agents represented by the formula:

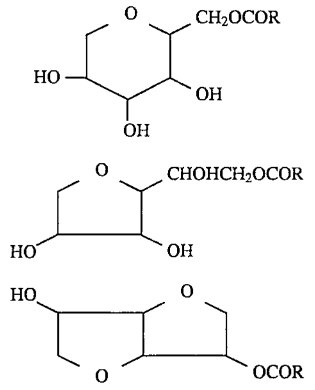

wherein R represents the fatty acid residues of the SPAN® 20., SPAN® 40 and SPAN® 80. SPAN® 20 contains the lauric acid residue. SPAN® 40 contains the palmitic acid residue. SPAN® 80 contains the oleic acid residue.

The SPAN® type materials are partial esters of the common fatty acids (lauric, palmitie, stearic, and oleic acid hexitol anhydrides (hexitans and hexides), derived from sorbitol.

Specific examples are sorbitan monolaurate, monooleate, monopalmitate, monosterate. Diesters and triesters of sorbitan are also suitable.

Materials used in the examples were:

Durkey® D17 partial hydrogenated soybean oil as the fat.

Certain compositions of fat/surfactant were added to powdered laundry detergent and improvements in substantivity of fragrance on wet laundry were observed. All tests were conducted with panels of 18 to 20 people. Control samples were prepared by adding 0.3% fragrance to the laundry detergent base and tumbling in a Turbula mixer until the fragrance was fully dispersed. Carrier samples were prepared by blending the appropriate amount of carrier with laundry detergent to yield 0.3% fragrance then tumbling in the Turbula mixer. Washes were made on a laundrometer at 37° C. with one wash and one rinse cycle.

Samples of "reference" and "sample" were presented to each panelist and they were asked to compare the fragrance intensity of the reference to the sample and indicate if the sample is:

1 much stronger;

2 stronger;

3 slightly stronger;

4 same;

5 slightly weaker;

6 weaker;

7 much weaker; than the reference.

Results were tabulated by dividing the number of stronger responses by the total of responses to yield "% stronger".

In the panel tests, significant increases in substantivity on white polyester/cotton (70/30) cloth were obtained using carriers formed of Fat/Span® 40/Fragrance in the proportion of 60/20/20% by weight. Good results were also observed with formulations wherein these proportions were changed to 40/40/20% by weight.

The fragrance components were combinations of proprietary materials identified as "a citrus type laundry fragrance" and a "floral type laundry fragrance".

Laundry bases used in these tests were:

1 Powdered detergent with phosphate, inorganic bleach and TAED bleach activator;

2 Powdered detergent containing phosphate;

3 Powdered detergent containing nonionic surfactant and zeolite.

Although not wishing to be bound by any theory, applicants believe that when washing, the fat protects the fragrance from being removed from the wash water by the detergent. The surfactant provides a slow emulsification of the fat/fragrance which allows interaction and deposition of the fragrance on the clothes. This deposition is possible due to the Van den Waals bonding between the fat and the clothes.

Fourteen week stability tests were also carried out on this samples and were found to be stable in the above bases and in some cases with improved fragrance stability.

The panel testing procedures are described in the following examples:

EXAMPLE 1

The samples prepared were tested for effectiveness. A group panel test was organized consisting of 5 people.

The laundry samples were prepared at a 0.3% effective fragrance concentration using a citrus type laundry fragrance.

Fabric swatches were 65/35 Polyester/cotton

Four (4) pieces of 3"×3" fabric swatches were placed in one liter Launderometer canisters with steel ball bearings.

750 ml of water was added. The detergent and carrier was added to each canister and sealed. In addition, an oil on detergent reference was also used.

The group test panel results revealed that the samples containing the Fat/surfactant (Span® 40) performed better than the others.

Samples evaluated in this example were as follows:

1. Oil adsorbed on detergent
2. Fat/Myverol®/Fragrance (60/20/20)
3. PEG 8000/Fragrance (80/20)
4. Fat/Span® 40/Fragrance (60/20/20)
5. Fat/Span® 40/Fragrance (40/40/20)
6. Fat/Tween® 20/Fragrance (60/20/20)

The loading of fragrance at 0.3% was run in 1 liter canisters in the launderometer with:

750 ml water—wash—30 minutes 750 ml water—rinse—15 minutes

The damp swatches were placed into labeled 1 pint jars where they were rated by panelists.

Found that most rated #5 and #6 samples strongest compared to oil on detergent.

EXAMPLE 2

Purpose: To determine which carriers perform better in comparison to oil-on-detergent reference in a panel test with expert judges

| Carrier | Description |
|---|---|
| 0743-1-A | Fat/Span ®40/Fragrance (40/40/20) |
| 0693-1-A | Fat/Myverol ®/Fragrance (60/20/20) |
| 0743-1-B | Fat/Span ®40/Fragrance (60/20/20) |
| 0693-1-B | PEG8000/Fragrance (80/20) |

Fragrance—Citrus Type Laundry Fragrance

Detergent Base—Commercial

Fragrance Loading—0.3%

Sample Preparation

1. Weighed 0.032 g of carrier onto 2.23 g of detergent base, mixed thoroughly.
2. Prepared 200 g of detergent/oil using 0.6 g fragrance using Turbula mixer for ½ hour.

Cloth 65/35 Polyester/Cotton swatches/

Following is a table of panelist responses comparing each carrier to oil on detergent reference.

| | 0743-1A | 0693-1A | 0743-1-B | 0693-1-B |
|---|---|---|---|---|
| Total weaker | 7 | 13 | 4 | 13 |
| Much weaker | 1 | 2 | 0 | 4 |
| Moderately weaker | 5 | 2 | 2 | 3 |
| Sightly weaker | 1 | 9 | 2 | 6 |
| No difference | 0 | 2 | 1 | 2 |
| Total stronger | 16 | 8 | 11 | 2 |
| Slightly stronger | 9 | 7 | 6 | 1 |
| Moderately stronger | 6 | 1 | 4 | 1 |
| Much stronger | 1 | 0 | 1 | 0 |
| % Stronger | 70% | 38% | 73% | 13% |
| Total Panelists | 23 | 23 | 16 | 17 |

The results show that the two carriers containing Span® 40 and fat produced higher sensory intensity results. The Fat/Myverol® and PEG 8000 system did not perform well.

EXAMPLE 3

Purpose: To evaluate aroma deposition on laundered cloth using carriers.

| | |
|---|---|
| Carrier: | 0693-1-A Fat/Myverol ®/Fragrance (60/20/20) |
| | 0813-1 Sipernat ®22/Fragrance/Fat (40/40/20) |

0813-1 was prepared by adsorbing fragrances on Sipernat®22 silica and coating with fat on a fluid bed coater.

Fragrance—Citrus Type Laundry Fragrance

Detergent—with bleach and TAED

The detergent base was switched to determine if bleach and TAED influenced carrier performance. Table of panelists' responses, comparing each sample to oil on detergent reference

| | 0693-1-A | 0813-1 |
|---|---|---|
| Total weaker | 4 | 13 |
| Much weaker | 1 | 3 |
| Moderately weaker | 1 | 4 |
| Slightly weaker | 2 | 6 |
| No Difference | 0 | 3 |

-continued

| | 0693-1-A | 0813-1 |
|---|---|---|
| Total Stronger | 17 | 5 |
| Slightly Stronger | 9 | 3 |
| Moderately stronger | 5 | 1 |
| Much stronger | 3 | 1 |
| % Stronger | 74% | 25% |
| Total | 23 | 20 |

The results show sample 0693-1-A Fat/Myverol® system performed better on the detergent base containing bleach and TAED then the previous run using the non bleach detergent.

EXAMPLE 4

Carriers fabricated containing Sipernat® 22 brand silica, fragrance and fat were run previously as carriers. These materials did not perform very well. A carrier containing Sipernat® 22 and fragrance, coated with Fat/Span® 40 should provide comparison between solid matrix and coated product.

| Materials | |
|---|---|
| 0833-4 | 20% Sipernat ® 22<br>40% Fragrance Citrus type<br>40% Fat/Span ® 40 |

This carrier was run on both bleach and non-bleach detergent bases and compared with oil-on-detergent references. This was also compared with solid drum chilled Fat/Span®40/Fragrance which has been shown to be effective.

Prepared cloth (damp) and submitted to STC judges for evaluation.

| | 0833-4/no bleach | 0833-4/with bleach |
|---|---|---|
| Total weaker | 18 | 2 |
| Much weaker | 2 | 0 |
| Moderately weaker | 7 | 0 |
| Slightly weaker | 9 | 2 |
| No Difference | 1 | 5 |
| Total Stronger | 2 | 14 |
| Slightly Stronger | 2 | 8 |
| Moderately Stronger | 0 | 5 |
| Much Stronger | 0 | 1 |
| % Stronger | 10% | 88% |
| Total Panelists | 21 | 21 |

Out of 21 evaluators who rated these two carriers, in comparison to oil-on-detergent, the carrier 0833-4 was significantly less effective in the detergent base without the bleach. This effect appears to indicate that the detergent base interaction with the carrier is significant as to effect the overall deposition profile on cloth. This was also evident in the test with the Fat/Myverol® carrier on both bases.

EXAMPLE 5

Re-evaluated the Fat Span® carrier is effective on the two detergent bases (with and without bleach):

| | | |
|---|---|---|
| Carrier | 0743-1-A | 60% Fat-Durkey 17<br>20% Span ® 40<br>20% Citrus Type Laundry Fragrance |
| System | Label | Description |
| Reference 1 | | 0.3 Fragrance in Bleach Base |
| Sample 1 | | 0743-1-A carrier in Bleach Base |
| Reference 2 | | 0.3% Fragrance in Non-bleach Base |
| Sample 2 | | 0743-1-A carrier in Non-Bleach Base |

The following table lists responses of the panelists, comparing odor intensity of each carrier vs. oil on detergent on damp cloth in a pair comparison test.

| | 0743-1A/ bleach | 0743-1A/ no bleach | 0743-1A/ bleach | 0743-1A/ no bleach |
|---|---|---|---|---|
| Total weaker | 1 | 8 | 0 | 2 |
| Much weaker | 0 | 0 | 0 | 0 |
| Moderately weaker | 0 | 1 | 0 | 1 |
| Slightly weaker | 1 | 7 | 0 | 1 |
| No difference | 1 | 4 | 0 | 1 |
| Total stronger | 20 | 10 | 22 | 19 |
| slightly stronger | 5 | 5 | 4 | 7 |
| Moderately stronger | 8 | 4 | 8 | 5 |
| Much Stronger | 7 | 1 | 10 | 7 |
| % Stronger | 95% | 56% | 100% | 95% |
| TOTAL EVALUATIONS | 22 | 22 | 22 | 22 |

The results above show for the damp cloth tested on the bleach base, a consistent positive response by the 22 judges. However, the non bleach base with the same carrier produced a wider distribution in panelist responses but were still overall positive.

EXAMPLE 6

The previous test showed positive results for sample using carrier 0743-1-A on the bleach base. The non-bleach base has been some concern because of the lack of repeatable results. This test repeats the carrier 0743-1A on non-bleach base with two sets of panelists. In addition, repetition of the Fat/Fragrance system in carrier 0693-1-A on the bleach base was done.

Both carriers contained 20% Citrus type Laundry Fragrance at 0.3% loading.

| Label | Description |
|---|---|
| Reference 1 | 0.3% Fragrance on Non-bleach Base |
| Sample 1 | carrier 0743-1-A on Non-bleach Base |
| Reference 2 | 0.3% Fragrance on Bleach Base |
| Sample 2 | carrier 0693-1-A on Bleach Base |

| | 0743-1A/ Non-Bleach | 0693-1A/ Bleach | 0743-1A/ Non-Bleach | 0693-1-A/ Bleach |
|---|---|---|---|---|
| Total weaker | 3 | 9 | 5 | 5 |
| Much weaker | 1 | 1 | 0 | 0 |
| Moderately weaker | 0 | 5 | 0 | 1 |
| Slightly weaker | 2 | 3 | 5 | 4 |
| No difference | 4 | 3 | 2 | 1 |
| Total stronger | 17 | 12 | 15 | 16 |
| slightly stronger | 7 | 8 | 7 | 11 |
| Moderately stronger | 7 | 3 | 6 | 3 |
| Much Stronger | 3 | 1 | 2 | 2 |

-continued

| | 0743-1A/ Non-Bleach | 0693-1A/ Bleach | 0743-1A/ Non-Bleach | 0693-1-A/ Bleach |
|---|---|---|---|---|
| % Stronger | 17/20 | 12/21 | 15/20 | 16/21 |
| TOTAL EVALUATIONS | 24 | 24 | 22 | 22 |

Compositions were prepared with many fragrances as well as the following aroma chemicals:

LINALYL ACETATE
ALDEHYDE C
HEXYL CINNAMIC ALDEHYDE
CITRAL VA®
HEXYL SALICYLATE
HELIONAL
AMYL SALICYLATE
LILIAL
ALLYL AMYL GLYCOLATE
FLORAL POWDER BQT
ORANGE OIL
METHYL NONYL ACETALDEHYDE
PHENYL ETHYL ALCOHOL
DIHYDRO MYRCENOL
LYCL ACETATE
HEDIONE
ISO E SUPER®
TETRA HYDRO LINALOOL
DIHYDRO TERDINEOL
GALAXOLIDE

As employed herein and in appended claims the term "perfume" is used in its ordinary sense to refer to and include any essentially water insoluble fragrant substance or mixture of substances including natural (i.e., obtained by extraction of flowers, herbs, leaves, roots, barks, wood, blossoms or plants), artificial (i.e., a mixture of different nature oils or oil constituents) and synthetic (i.e., synthetically produced) odoriferous substances. Such materials are often accompanied by auxiliary materials, such as fixatives, extenders and stabilizers. These auxiliaries are also included within the meaning of "perfume", as used herein. Typically, perfumes are complex mixtures of a plurality of organic compounds, which may include odoriferous or fragrant essential hydrocarbons, such as terpenes, ethers and other compounds which are of acceptable stabilities in the present compositions. Such materials are either well known in the art or are readily determinable by simple testing, and so need not be listed in detail here.

The perfumes employed in the invention will preferably be of a polar nature and lipophilic, so that they form at least a significant part of the oil phase of the micro-emulsion. Such perfumes will be hypochlorite-stable, of course, and it has been noted that the best perfumes for this purpose are those which are in the following olfactory families: floral, including floral, green floral, woody floral and fruity floral; chypre, including floral aldehydic chypre, leather chypre and green chypre; fougere; amber, including floral woody amber, floral spicy amber, sweet amber and semi-floral amber; and leather.

Perfume components and mixtures thereof which can be used for the preparation of such perfumes may be natural products such as essential oils, absolutes, resinoids, resins, etc., and synthetic perfume components such as hydrocarbons, alcohols, aldehydes, ketones, ethers, acids, esters, acetals, ketals, nitriles, etc., including saturated and unsaturated compounds, aliphatic, carbocyclic and heterocyclic compounds. Examples of such perfume components are geraniol, geranyl acetate, linalool, linaly acetate, tetrayhdrolinalool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, benzyl benzoate, styrallyl acetate, amyl salicylate, dimethylbenzylcarbinol, trichloromethylphenylcarbinyl methylphenylcarbinyl acetate, p-tert-butyl-cyclohexyl acetate, isononyl acetate, vetiveryl acetate, vetiverol, alpha-n-amylcinammic aidehyde, alpha-hexyl-cinammic aidehyde, 2-methyl-3-(p-tert-butylphenyl)-propanal, 2-methyl-3-(p-isopropyl-phenyl)propanal, 3-(p-tert.butylphenyl)propanal, tricyclodecenyl acetate, tricyclodecenyl propionate, 4-(4-hydroxy- 4-methylpentyl)-3-cyclohexenecarbaldehyde, 4-(4-methyl- 3-pentenyl)-3-cyclohexenecarbaldehyde, 4-acetoxy- 3-pentyltetrahydropyran, methyl dihydrojasmonate, 2-n-heptylcyclopentanone, 3-methyl-2-pentyl-cyclopentanone, n-decanal, n-dodecanal, 9-decenol-1, phenoxyethyl isobutyrate, phenylacetaldehyde dimethyl acetal, phenylacetaldehyde diethyl acetal, geranonitrile, citronellonitrile, cedryl acetal, 3-isocam-phylcyclohexanol, cedryl methyl ether, isolongifolanone, aubepine nitrile, aubepine, heliotropine, coumarin, eugenol, vanillin, diphenyl oxide, hydroxycitronellal ionones, methyl ionones, isomethyl ionones, irones, cis-3-hexenol and esters thereof, indane musk fragrances, tetralin musk fragrances, isochroman musk fragrances, macrocyclic ketones, macrolactone musk fragrances, ethylene brassylate, aromatic nitro-musk fragrances. Suitable solvents, diluents or carriers for perfumes as mentioned above are for examples; ethanol, isopropanol, diethylene glycol monoethyl ether, dipropylene glycol, diethyl phthalate, triethyl citrate, etc.

Among the fatty components that can be used are the following:

Partially hydrogenated vegetable oils for use in peanut butter (stabilizers), bread production, shortening manufacture, chewing gum bases, icings (stabilizer), dry mix, encapsulation, caramel coatings and as a general purpose stabilizing hard fat.

| | Stearine 07 | Stearine 17 | Stearine 27 | K.L.X |
|---|---|---|---|---|
| Label Ingredient Statement | Partially Hydrogenated Cottonseed Oil | Partially Hydrogenated Soybean Oil | Partially Hydrogenated Palm oil | Partially Hydrogenated Cottonseed, Soybean Oil |
| Color | 4.0 R (Max) | 3.0 OR (Max.) | 5.)R (Max.) | 2.5 R (Max.) |
| Free Fatty Acids | 0.10% (Max.) | 0.10% (Max.) | 0.10% (Max.) | 0.10% (Max.) |

-continued

| | Stearine 07 | Stearine 17 | Stearine 27 | K.L.X |
|---|---|---|---|---|
| Iodine Value | 4.0 (Max.) | 4.0 (Max.) | 5.0 (Max.) | — |
| Capillary Melting Point | 141–147° F.2 | 152–158° F. | 136–144° F. | 124–130° F. |
| Odor/Flavor | Bland | Bland | Bland | Bland |
| A.O.M. | — | — | — | 200 hours (MIN.) |
| Typical Solid Fat Index | | | | |
| 50° F. | | NOT APPLICABLE | | 80 |
| 70° F. | | | | 80 |
| 80° F. | | | | 80 |
| 92° F. | | | | 80 |
| 100° F. | | | | 77 |
| 110° F. | | | | 62 |
| Package/Form | Beads in 50 lb. Cartons, Flakes in 50 lb. cartons | Flakes in 50 lb. cartons | Beads in 50 lb. Cartons Flakes in 50 lb. cartons | Flakes in 50 lb. cartons |

MYVEROL® 1806 is a distilled monoglyceride prepared by the interestification of propylene glycol with fully hydrogenated soybean oil followed by molecular distillation. Typical properties are:

| Type | Fat Source | Monoester Content, Min % | Propylene Glycol Content, Max % | Acid Value, Max | Iodine Value, Max | Specific Gravity at 80° C. | Melting Point, Approx. °C. (°F.) | Physical Form |
|---|---|---|---|---|---|---|---|---|
| 1806 | Hydrogenated Soybean oil | 90 | 1.2 | 3 | 5 | 0.92 | 69 (156) | Small Beads |

We claim:

1. A method for producing a fragrance-containing solid particle of improved substantivity for incorporation into laundry detergents consisting essentially of:

(i) selecting a fat component selected from the group consisting of partially hydrogenated soybean oil, partially hydrogenated cotton seed oil and partially hydrogenated palm oil;

(ii) heating said fat component to an elevated temperature sufficient to form a first molten melt thereof;

(iii) selecting a solid surface active agent selected from the group consisting of a SPAN® surfactant of HLB 4.3 to 8.6, said SPAN® surfactant being defined as a mixture of compounds having the structure:

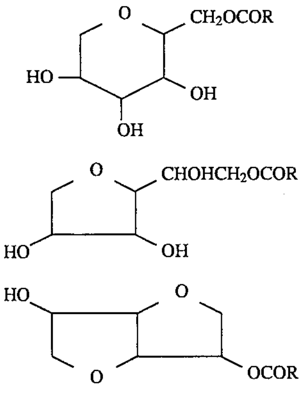

wherein R is $C_{11}$–$C_{17}$ alkyl or alkenyl;

(iv) heating said surface active agent to form a second molten melt thereof;

(v) combining said first and second melts with an aroma chemical and uniformly dispersing said aroma chemical in the combined melt of said fat component and said surfactant;

(vi) rapidly cooling said melts to form a solid material containing said fat component, said nonionic SPAN® surfactant and aroma chemical; and (vii) forming solid particles thereof to obtain a fragrance containing particulate aroma chemical carrier, wherein said fat component is present in the amount of 40 to 99% by weight, said surface active agent is present in the amount of 1 to 60% by weight and said aroma chemical is present in an amount of 1 to 40% by weight based on 100 parts by weight of combined said fat component and said surface active agent.

2. The method according to claim 1 wherein said fat component is partially hydrogenated soybean oil.

3. A fragrance-containing solid particle of improved substantivity for incorporation into laundry detergents consisting essentially of:

(i) a fat component selected from the group consisting of partially hydrogenated soybean oil, partially hydrogenated cotton seed oil and partially hydrogenated palm oil;

(ii) a solid surface active agent selected from the group consisting of a of a SPAN® surfactant of HLB 4.3 to 8.6, said SPAN® surfactant being defined as a mixture of compounds having the structure:

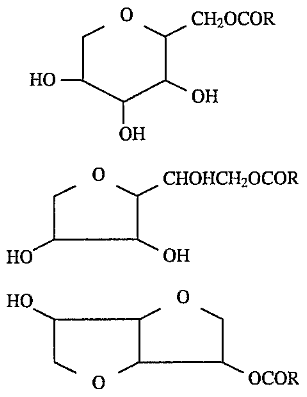

wherein R is $C_{11}$–$C_{17}$ alkyl or alkenyl;

(iv) heating said surface active agent to form a second molten melt thereof;

(v) combining said first and second melts with an aroma chemical and uniformly dispersing said aroma chemical in the combined melt of said fat component and said surfactant;

(vi) rapidly cooling said melts to form a solid material containing said fat component, said nonionic SPAN® surfactant and aroma chemical; and (vii) forming solid particles thereof to obtain a fragrance containing particulate aroma chemical carrier, wherein said fat component is present in the amount of 40 to 99% by weight, said surface active agent is present in the amount of 1 to 60% by weight and said aroma chemical is present in an amount of 1 to 40% by weight based on 100 parts by weight of combined said fat component and said surface active agent.

* * * * *